United States Patent [19]

Lescrenier

[11] 4,255,657
[45] Mar. 10, 1981

[54] DIVERGING PLANE POSITIONING DEVICE

[76] Inventor: Charles Lescrenier, 660 Crescent Ct., Wautatosa, Wis. 53213

[21] Appl. No.: 45,636

[22] Filed: Jun. 5, 1979

[51] Int. Cl.³ .............................................. G03B 41/16
[52] U.S. Cl. ..................................... 250/322; 250/491
[58] Field of Search ........................ 250/491, 322, 312

[56] References Cited

U.S. PATENT DOCUMENTS

| 2,486,866 | 11/1949 | Morgan et al. | 250/322 |
| 2,829,273 | 4/1958 | Fransen | 250/322 |
| 3,708,663 | 1/1973 | Biederman | 250/312 |
| 4,117,337 | 9/1978 | Staats | 250/491 |

Primary Examiner—Alfred E. Smith
Assistant Examiner—T. N. Grigsby
Attorney, Agent, or Firm—Andrus, Sceales, Starke & Sawall

[57] ABSTRACT

A device for positioning the spinal column of a patient with respect to exposure control devices behind a chest X-ray film sheet has a light source generating a plane of light bearing a fixed relationship to the exposure control devices. The plane forms a luminous line on the patient when the patient steps in the path of the plane which may be used for positioning as by placing the patient's spinal column along the line. The other planes of light may be used to define the edges of the X-ray film sheet.

11 Claims, 4 Drawing Figures

DIVERGING PLANE POSITIONING DEVICE

BACKGROUND OF THE INVENTION

1. Field of the Invention

The present invention relates to a positioning device suitable for positioning a body adjacent a contiguous target area.

2. Description of the Prior Art

Chest X-rays are a basic diagnostic tool for treating diseases or injuries of the thorax. To obtain a chest X-ray, the patient typically stands in front of a film holder containing a sheet of film sufficiently large to extend from the neck to the diaphragm and to each side of the chest. The patient is then exposed to radiation to obtain an X-ray image on the film.

It is well recognized that the diagnostic effectiveness of a chest X-ray depends in great measure on the proper positioning of the patient. It is important that the patient be centered on the film sheet.

For this purpose, various types of positioning apparatii are in use. One such apparatus shines a pattern of light along the axis of the radiation beam onto the patient. The pattern of light has a frame, cross-hairs or other aiming means for positioning the patient, film holder, and X-ray generator. Another type of apparatus uses lines of light to indicate the edges of the film sheet.

Because of concern over the health hazards of X-rays, exposure control devices have come into use. These devices may typically be ionization chambers positioned behind the X-ray film sheet for alignment with the lung fields of the patient. When a predetermined amount of radiation has been received by the exposure control devices, exposure is automatically terminated.

Problems have heretofore arisen with automatic exposure control systems when used with existing positioning systems due to improper positioning of the patient. When taking a posterior-anterior chest X-ray, the spinal column of the patient may become located over one of the exposure control devices. The density of the spinal column is greater than that of the lungs so that the operation of the exposure control device is altered, typically resulting in over exposure of the film. Not only is the patient over exposed on the initial chest X-ray, this over exposure often requires a retake, further increasing the amount of radiation to which the patient is exposed.

SUMMARY OF THE PRESENT INVENTION

The present invention comprises a positioning device suitable for positioning a patient with respect to an X-ray film sheet and particularly with respect to associated exposure control devices. Improper positioning of the patient, which may result in improper exposure, can be quickly and positively identified.

The device of the present invention includes a light source generating a plane of light. The light source is so arranged that the light plane bears a known relationship to the exposure control devices. The light plane is typically centrally aligned with the exposure control devices. The light source may also generate planes of light defining the vertical edges of the film sheet.

When the patient steps in front of the film sheet, the plane appears as a luminous line on his/her body. For a frontal chest X-ray, the central vertical light plane is aligned with the spine to insure that the spinal column does not block the exposure control devices and the lung fields are positioned over the devices. If provided, the outer two light planes may be aligned generally with the sides of the chest or armpits. Any improper positioning may be easily seen by the improper location of the lines on the patient's body. The central light plane may also be used to position the patient for lateral X-rays. In this case, the patient is positioned so that the central luminous line lies along the central frontal plane of the body.

DETAILED DESCRIPTION OF THE PREFERRED EMBODIMENT

Figure 1:
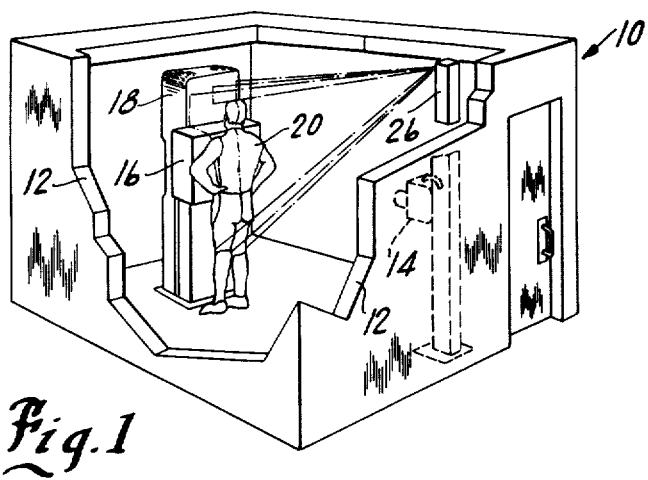
FIG. 1 is a perspective view of the positioning device of the present invention in use with chest X-ray apparatus.

FIG. 1 shows X-ray room 10 having radiation absorbing walls 12 providing the customary shielding. X-ray generator 14 is provided in room 10 for generating a generally horizontal X-ray beam, the axis of which is centered on film holder 16. Film holder 16 is mounted on stand 18 for exposure to the X-ray beam. Patient 20 stands in front of film holder 16 during exposure.

Figure 3:
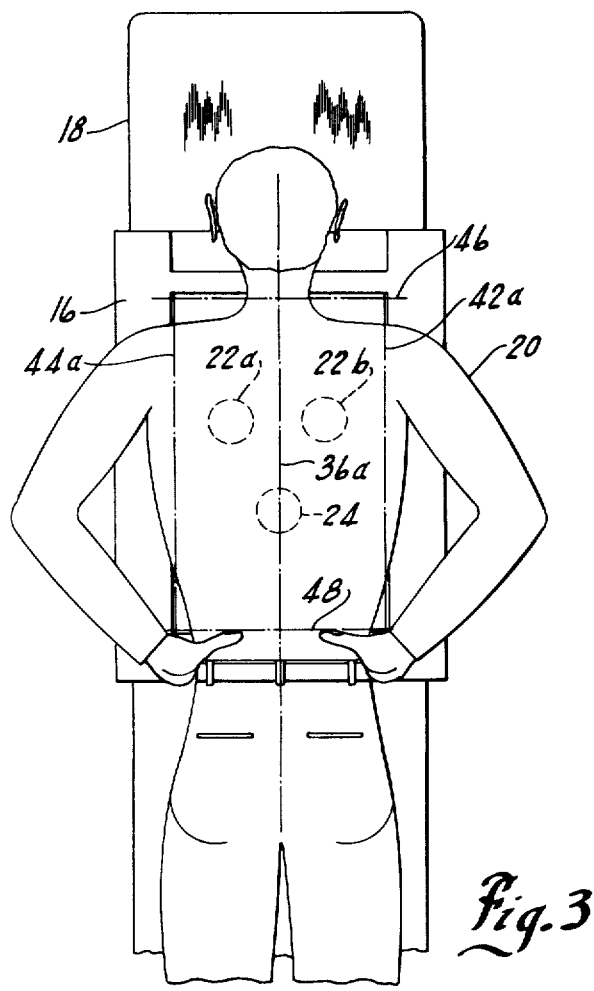
FIG. 3 is a rear view of the positioning device in use to take a posterior-anterior X-ray.
Figure 4:
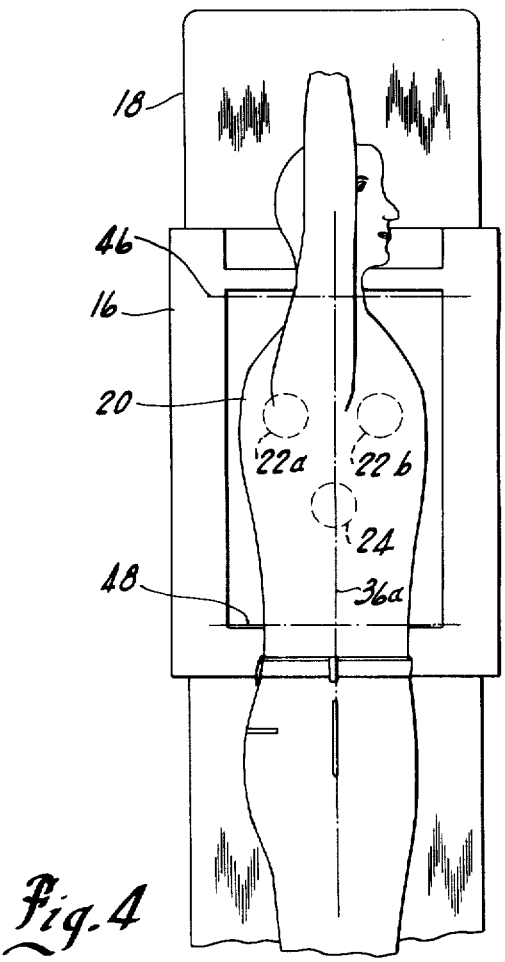
FIG. 4 is a side view of the positioning device of the present invention in use to take a lateral X-ray.

As shown most clearly in FIGS. 3 and 4, exposure control devices are mounted in holder 16 behind the sheet of film. Exposure control devices 22a and 22b are positioned to lie in the lung fields of patient 20 when the patient faces the film holder. Exposure control device 24 is positioned so as to lie in the lung field of patient 20 when the patient stands sideways with respect to film holder 16.

FIG. 1 also shows the positioner 26 of the present invention. Positioner 26 is located in proximity to X-ray generator 14 and generates at least one plane of light extending in the same direction as the X-ray beam of the generator.

Figure 2:
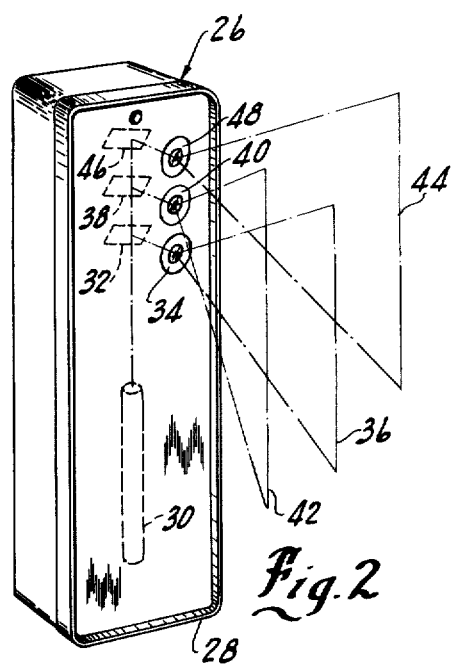
FIG. 2 is a perspective view of the positioning device of the present invention.

FIG. 2 shows positioner 26 in detail. Positioner 26 includes cabinet 28 containing a light emitter, such as laser 30. The light emitted from laser 30 strikes half-silvered mirror 32. From mirror 32, the light travels through anamorphic lens or line generator 34 which forms the beam of light from the laser into diverging rays which lie in a single plane 36. If desired, the light passing through half-silvered mirror 32 may be applied to other half-silvered and fully-silvered mirrors and other anamorphic lenses to produce the planes of light defining the edges of the film sheet. Specifically, the light passing through half-silvered mirror 32 strikes half-silvered mirror 38, to provide a beam which anamorphic lens 40 employs to produce light plane 42. The light passing through mirror 38 provides light plane 44 through mirror 46 and lens 48.

Light planes 36, 42, and 44 are parallel to each other with planes 42 and 44 diverging on each side of central plane 36 in a direction away from positioner 26. The divergence required of light planes 42 and 44 may be obtained by altering the position of mirrors 38 and 46 or lenses 40 and 48 in positioner 26.

While it is preferable that the planes of light be visible, it will be appreciated that other types of radiant energy, such as infrared; other types of sources, such as incandescent; or other types of line generators, such as an aperture, may be used. The foregoing terms are intended to include all suitable types and sources of radiant energy and line generators.

Positioner 26 is so positioned on the wall 12 of room 10 that light plane 36, is projected on film holder 16 and bears an established relationship to the film holder and particularly to, exposure control devices 22 and 24 located behind the film. Typically, light plane 36 will lie along the vertical central axis of the film sheet. It will thus be centered on exposure control device 24 and be equidistant from devices 22a and 22b. Diverging planes 42 and 44 lie along the outer vertical edges of the film sheet.

As shown in FIG. 3, light plane 36 forms a luminous line 36a where it strikes the body of patient 20. This line may be used to align the patient with exposure control device 22a and 22b as by placing line 36a along the spinal column of patient 20, thereby insuring that the spinal column does not lie over either of exposure control devices 22a or 22b used for a posterior-anterior X-ray. Light planes 42 and 44 are aligned generally with the sides of the chest or armpits as evidenced by lines 42a or 44a. Any improper positioning, twisting, or shifting may be easily seen by the improper location of lines 36a, 40a, and 44a on the patient's body, or by the lack of symmetry of the lines.

If it is desired to make a side X-ray of the chest, the patient 20 is turned 90° from the position shown in FIG. 3 and positioned as shown in FIG. 4 so that line 36a runs down the center of the side of the chest. The patient will then be properly positioned with respect to exposure control device 24 so that the spinal column does not block the exposure control device.

If desired, positioner 26 may include means to generate horizontal light planes which define the upper and lower edges of the film sheet, as shown in FIG. 4 by lines 46 and 48. Light source 30 may be modified to generate the two additional light planes or a separate light source similar to light source 30 may be employed. This modification can be used to particular advantage in installations in which film holder 16 is fixed in location and the patient stands on a movable lift for positioning.

Various modes for carrying out the invention are contemplated as being within the scope of the following claims particularly pointing out and distinctly claiming the subject matter which is regarded as the invention.

I claim:

1. A device for positioning the spinal column of a patient located in front of an X-ray film sheet with respect to exposure control means located behind the film sheet, said device comprising a light source having means for generating a first plane of light appliable to the front of the film sheet and the spinal column of the contiguous patient and which bears a known relationship to the exposure control means, said light source further having means for generating a pair of additional light planes diverging in a direction towards the film sheet with respect to the first plane of light.

2. The device according to claim 1 wherein a single exposure control device is located behind the film sheet and wherein said light source is further defined as having means for generating a first plane of light centered on the exposure control device.

3. The device according to claim 1 wherein said diverging light plane generating means is further defined as generating a pair of light planes defining the edges of the film sheet.

4. The device according to claim 1 or 3 wherein said light source is further defined as having means for generating a further pair of additional light planes lying normal to said first plane of light for defining the upper and lower edges of the film sheet.

5. The device according to claim 1 wherein a pair of horizontally spaced exposure control devices are located behind the film sheet and wherein said light source is further defined as having means for generating a vertical first plane of light lying equidistant between the pair of spaced exposure control devices.

6. The device according to claim 5 wherein an additional exposure control device is located behind the film sheet and wherein the light source is further defined as having means for generating a first vertical plane of light centered on the additional exposure control device.

7. Apparatus for obtaining patient-X-rays comprising:
an X-ray generator providing a beam of X-ray radiation;
a film sheet positioned in the path of said radiation and having exposure control means located behind the sheet for controlling X-ray exposure responsive to received radiation; and
a device for positioning the spinal column of a patient located in front of the film sheet with respect to the exposure control means, said device comprising a light source having means for generating a first plane of light appliable to the front of the film sheet and the spinal column of the contiguous patient and which bears a known relationship to the exposure control means, said light source further having means for generating a pair of additional light planes diverging in a direction toward the film sheet with respect to the first plane of light.

8. The apparatus according to claim 7 wherein said exposure control means includes a pair of horizontally spaced exposure control devices behind the sheet of film and wherein said light source is further defined as having means for generating a vertical first plane of light lying equidistant between the pair of spaced exposure control devices.

9. The apparatus according to claim 7 wherein an additional control device is located behind the film sheet and wherein the light source is further defined as having means for generating a vertical first plane of light centered on the additional exposure control device.

10. The apparatus according to claim 7 wherein said additional light plane generating means is further defined as means for generating a pair of additional planes defining the edges of the film sheet.

11. The apparatus according to claim 7 or 10 wherein said light source is further defined as having means for generating a second pair of additional light planes for defining all four edges of the film.

* * * * *